United States Patent [19]
Kemp et al.

[11] Patent Number: 5,256,418
[45] Date of Patent: Oct. 26, 1993

[54] COLLAGEN CONSTRUCTS

[75] Inventors: Paul D. Kemp, Cambridge; Robert M. Carr, Jr., Boston; John G. Maresh, Cambridge, all of Mass.

[73] Assignee: Organogenesis, Inc., Canton, Mass.

[21] Appl. No.: 505,678

[22] Filed: Apr. 6, 1990

[51] Int. Cl.$^5$ .......................... A61F 2/28; A61K 9/14; A61K 37/12; C07K 15/20

[52] U.S. Cl. .................... 424/423; 424/422; 424/426; 424/456; 424/484; 424/485; 424/491; 424/492; 623/11; 623/12; 623/16; 623/901; 128/658

[58] Field of Search ............... 424/422, 423, 426, 456, 424/484, 485, 491, 492; 514/2, 12, 774, 944; 623/11, 12, 16, 901; 128/658; 530/353, 355, 356

[56] References Cited

U.S. PATENT DOCUMENTS

| | | | |
|---|---|---|---|
| 2,598,608 | 5/1952 | Salo et al. | 530/356 |
| 2,637,321 | 5/1953 | Cresswell | 606/229 |
| 3,014,024 | 12/1961 | Lieberman et al. | 530/356 |
| 3,114,593 | 12/1963 | Grisset | 264/103 |
| 3,366,440 | 1/1968 | Nuwayser | 8/115.6 |
| 3,425,418 | 2/1969 | Chvapll et al. | 623/1 |
| 3,435,825 | 4/1969 | Thoennes | 606/229 |
| 3,502,534 | 3/1970 | Grisset | 156/344 |
| 3,587,586 | 6/1971 | Kronenthal | 606/154 |
| 3,644,202 | 2/1972 | Higley | 210/653 |
| 4,252,759 | 2/1981 | Yannas et al. | 264/86 |
| 4,319,363 | 3/1982 | Ketharanathan | 623/1 |
| 4,320,201 | 3/1982 | Berg et al. | 435/265 |
| 4,563,350 | 1/1986 | Nathan et al. | 623/16 |
| 4,620,327 | 11/1986 | Caplan et al. | 623/16 |
| 4,721,096 | 1/1988 | Naughton et al. | 128/898 |
| 4,787,900 | 11/1988 | Yannas | 623/1 |
| 4,789,663 | 12/1988 | Wallace et al. | 623/16 |
| 4,863,732 | 9/1989 | Nathan et al. | 424/95 |
| 4,963,489 | 10/1990 | Naughton et al. | 435/240.1 |
| 4,980,403 | 12/1990 | Bateman et al. | 524/17 |
| 5,032,508 | 7/1991 | Naughton et al. | 435/32 |

FOREIGN PATENT DOCUMENTS

| | | |
|---|---|---|
| 0083868 | 12/1982 | European Pat. Off. . |
| 0243132 | 4/1987 | European Pat. Off. . |
| 0268421 | 11/1987 | European Pat. Off. . |
| 285471 | 10/1988 | European Pat. Off. . |
| 285474 | 10/1988 | European Pat. Off. . |
| WO88/08305 | 11/1988 | PCT Int'l Appl. . |

OTHER PUBLICATIONS

Patent Abstract from Derwent—EP 311305, Noishiki et al.

"Studies of the Mechanism of Hydrated Collagen Gel Reorganization by Human Skin Fibroblasts," C. Guidry & F. Grinnel, J. Cell Sci., 79, 67–81, (1985).

Mohamed, M. "Three-Dimensional Textiles," American Scientist, vol. 78, pp. 530–541.

Kato, et al., "Formation of Continuous Collagen Fibers: Evaluation of Biocompatibility and Mechanical Properties," Biomaterials, 1990, vol. 11, 169–75.

Organogenesis, Inc. 1990 Annual Report, published Mar. 29, 1991.

J. Ramshaw et al., "Precipitation of Collagens by Polyethylene Glycols," Analytical Biochemistry, 141:361–365 (1984).

Primary Examiner—Thurman K. Page
Assistant Examiner—Carlos Azpuru
Attorney, Agent, or Firm—David G. Conlin; Linda M. Buckley

[57] ABSTRACT

The present invention provides collagen constructs and methods of making and using such constructs. The present invention also provides tissue equivalents having improved characteristics and methods of making and using such tissue equivalents. This invention also provides methods of producing highly concentrated solutions of collagen.

34 Claims, 1 Drawing Sheet

FIG. 1  FIG. 2  FIG. 3  FIG. 4

COLLAGEN CONSTRUCTS

BACKGROUND

This invention relates to collagen constructs and to methods of making and using such constructs. This invention further relates to tissue equivalents having improved characteristics and to methods of making and using such tissue equivalents. This invention also relates to methods of producing highly concentrated solutions of collagen.

Collagen is usually found as the principal protein component of the extra-cellular matrix. In mammals, collagen sometimes constitutes as much as 60% of the total body protein. It comprises most of the organic matter of skin, tendons, bones and teeth, and occurs as fibrous inclusions in most other body structures. Collagen is a relatively weak immunogen, due in part to masking of potential antigenic determinants by the helical structure. This helical structure also makes collagen resistant to proteolysis. Collagen is a natural substance for cell adhesion and the major tensile load-bearing component of the musculo-skeletal system.

Because of the foregoing properties, collagen has applications in the manufacture of implantable prostheses, as a cell growth substrate, and in the preparation of living tissue equivalents. Much work has been done to develop collagen constructs for such applications, including constructs for use in research and development, tissue and organ repair and/or replacement. Collagen is the principal protein component of such collagen constructs.

Many methods are known for organizing collagen into constructs such as injectable pastes, living tissue equivalents, films, sponges and so forth. These methods include the formation of collagen fibrils for injectable pastes and blood vessel prosteheses, e.g., U.S. Pat. Nos. 4,252,759; 4,787,900; 4,319,363; and 3,425,418; the formation of collagen films, e.g., U.S. Pat. No. 3,014,024; and the formation of sponges, e.g., U.S. Pat. No. 4,320,201.

Another method of forming collagen constructs involves the contraction of collagen gels by a contractile agent, such as fibroblast cells, smooth muscle cells or blood platelets, to form living tissue equivalents.. Such tissue equivalents are disclosed in U.S. Pat. Nos. 4,485,096; 4,485,097; 4,539,716; 4,546,500; 4,604,346; 4,835,102; and 4,837,379 and co-pending application U.S. Ser. No. 07/252,249, filed Sep. 30, 1988, all of which are incorporated herein by reference (hereinafter collectively referred to as "the Patents"). These tissue equivalents include, but are not limited to, equivalents of epithelial tissue and connective tissue such as skin, cartilage, bone, blood vessels, and comprise living cells and extracellular matrix molecules, principally collagen, and may optionally be provided with components not typically found in normal tissue. Such tissue equivalents have a broad range of applications including applications in research and development, tissue and organ replacement and testing.

In these known methods, the collagen construct is organized from relatively dilute solutions of collagen, e.g., about 5-10 mg/ml, by air-drying or neutralizing. The collagen constructs which are produced by such methods typically have a sparse collagen density and few collagen/collagen interactions. These characteristics tend to decrease the structural integrity of such constructs. Moreover, many known methods of preparing collagen constructs also suffer the disadvantage of a lack of flexibility and in the degree of control over the process to form a construct having the desired shape.

It is highly desirable that the strength of such constructs be sufficient to enable ease of handling and to provide durability, particularly in applications which involve a significant mechanical handling or tensile or pulsatile stress. Accordingly, it is desirable to form collagen constructs which have a more dense fibrillar structure more akin to those found in vivo. It is believed that in vivo collagen is organized from very concentrated solutions. Thus, improved collagen constructs and methods of preparing such constructs are being sought.

SUMMARY OF THE INVENTION

The present invention provides collagen constructs and methods of making such collagen constructs. The collagen constructs of the present invention have improved properties including, increased strength and a dense fibrillar structure more akin to that found in vivo.

It has unexpectedly been discovered that collagen constructs can be formed at the interface of a collagen solution and a permeable member, the permeable member being in contact with an agent causing selective mass transfer of solvent from the collagen solution, e.g., in aqueous solutions the agent typically has a higher osmotic pressure than the collagen solution. For ease of reference, such agents shall hereinafter be referred to as "concentrating agents." While not wishing to be bound by theory, it is believed that in aqueous solution the construct is formed as the collagen concentrates by means of the development of an osmotic gradient at the permeable member.

In one preferred method of forming a construct comprising collagen in accordance with the present invention, the method comprises the steps of:

(a) providing a solution comprising collagen adjacent a permeable member, the permeable member being in contact with a concentrating agent; and (b) maintaining the collagen solution, permeable member and concentrating agent under conditions sufficient to enable the collagen construct to form at the permeable member.

Although constructs made by the foregoing method may have sufficient structural integrity for certain applications, an important aspect of the present invention is the formation of fibrils in the highly concentrated collagen constructs.

Accordingly, in another preferred embodiment the method described above comprises the additional step of causing fibrils to form in the collagen construct. Such fibrils may be caused to form as the collagen construct forms at the permeable member or they may be caused to form in the highly concentrated construct. It is believed that causing the fibrils to form after the collagen construct has reached a collagen concentration of about 50–100 mg/ml, provides constructs having a fibrillar organization of collagen more akin to that found in vivo than has heretofore been achieved. Fibril formation is caused by increasing the ionic strength of the concentrating agent, the pH or the temperature, or a combination thereof.

The methods of the present invention provide very concentrated collagen constructs solutions (in order of 100 mg/ml) in which can be caused to form a dense fibrillar structure more akin to those found in vivo. It appears that formation of fibrillar collagen constructs in accordance with the present invention is closer to the way collagen is organized in vivo than other known methods of forming collagen constructs. Apparently, collagen is organized in vivo from very concentrated collagen solutions which are very difficult to handle in vitro. Accordingly, the present invention also provides a method of concentrating a solution of collagen comprising:

(a) contacting a collagen solution with a permeable member, the permeable member being in contact with an agent for concentrating the collagen;

(b) maintaining the collagen solution and concentrating agent under conditions sufficient to enable the collagen solution to reach a concentration of from about 50 to 100 mg/ml. Although about 50 to 100 mg/ml is a preferred range, it is expected that collagen solutions of both higher and lower concentrations will be useful in certain applications.

The shape of collagen constructs in accordance with the present invention is determined in part by the permeable member. In one preferred embodiment, tubular collagen constructs are formed by use of a device having an inner and outer chamber, the interface between the inner and outer chamber comprising a tubular permeable member, the method comprising the steps of:

(a) providing a solution comprising collagen at a pH of about 2 to 4 to the outer chamber;

(b) providing a concentrating agent to the inner chamber; and (c) maintaining the collagen solution, permeable member and concentrating agent under conditions sufficient to enable the tubular collagen construct to form at the permeable member.

The methods of the present invention can be conveniently stopped and restarted. Accordingly, multi-layered collagen constructs are also provided by the present invention. Such constructs may be of any desired shape, flat and tubular constructs being preferred. In another preferred embodiment, a multi-layered tubular collagen construct is made by use of a device having an inner and outer chamber, the interface between the inner and outer chamber comprising a tubular permeable member, the method comprising the steps of:

(a) providing a first solution comprising collagen at a pH of about 2 to 4 to the outer chamber;

(b) providing a concentrating agent to the inner chamber;

(c) maintaining the first collagen solution, permeable member and concentrating agent under conditions sufficient to enable the tubular collagen construct to form at the permeable member;

(d) replacing the first collagen solution with a second solution comprising collagen; and (e) maintaining the second collagen solution, permeable member and concentrating agent under conditions sufficient to enable a second tubular construct to form outwardly of the first tubular construct; and (f) repeating steps (d) and (e) if additional layers of tubular collagen construct are desired.

This method allows for the possibility of changing the collagen mixture throughout to produce a collagen construct having a differing composition from one layer to the next, if desired. For example, a layer of controllable thickness containing angiogenic factors, anti-inflammatory agents, chemotatic agents, or collagenase inhibitors may be easily incorporated in multi-layer constructs of the present invention.

Particularly preferred collagen constructs provided by the present invention include living tissue equivalents which are different in organization from and offer advantages over the tissue equivalents disclosed in the Patents. Tissue equivalents made from collagen constructs as taught herein will be used hereinafter only to illustrate the present invention and are not intended to limit the present invention in any way.

In production of tissue equivalents in accordance with the Patents, collagen gels to produce short, thin fibrils which are concentrated through contraction of the gel by a contractile agent. The resulting tissue equivalent has a sparser collagen density and fewer collagen/collagen interactions than tissue equivalents in accordance with the present invention.

While tissue equivalents produced in accordance with the Patents are acceptable for many applications, it is desirable to have tissue equivalents of increased strength for certain applications. Accordingly, the tissue equivalents of the present invention which are prepared by use of collagen constructs formed from highly concentrated collagen solutions and offer improved strength are preferred for certain applications, e.g., applications wherein the tissue equivalent is subject to tensile or pulsatile stress.

Materials used to prepare the tissue equivalents as taught by the present invention may optionally include fibrinogen; an agent such as thrombin, which causes the formation of fibrin from fibrinogen; fibrin; an agent, such as Factor XIII, which causes the fibrinogen and collagen to cross-link; one or more contractile agents; living cells; nutrient media; and additives.

The configuration of apparatus for use the present invention will depend upon the type of collagen construct made, as well as the intended use thereof.

Tissue equivalents made in accordance with the present invention are generally cast as flat sheet, a hollow tube or a network of hollow tubes. However, they can be cast in any desired shape. For example, in some embodiments of the present invention, it is desirable to change the natural geometry of the tissue equivalent. For example, skin tissue equivalent may be cast as a cylinder rather than as a sheet and the layers of blood vessel tissue equivalent may be cast in the reverse of the order of natural blood vessels.

Although living tissue equivalents formed by use of the collagen constructs of the present invention are formed by a method different from that disclosed in the Patents, general methods of forming layered tissue equivalents, providing cells for such tissue equivalents and apparatus disclosed in the Patents are useful in the practice of the present invention. For example, human blood vessel tissue equivalents which comprise multi-layered tubes made by use of collagen gels and cultured vascular cells are disclosed in U.S. Pat. Nos. 4,539,716 and 4,546,500 and the methods taught therein are generally applicable in the methods of the present invention.

Blood vessel tissue equivalents made by use of the present invention can be made for different types of blood vessels by using cells cultured from the appropriate sources. Arterial blood vessel tissue equivalents further comprise cells cultured from the corresponding layers of an artery. Capillary blood vessel equivalents further comprise capillary endothelial cells and pericytes in place of the adventitial fibroblasts. Venous blood vessel tissue equivalent further comprise cells cultured from veins and are fabricated with thinner outer layers than arterial blood vessel tissue equivalents. For the studies of certain diseases, cells cultured from patients with the particular disease are incorporated into the blood vessel tissue equivalent.

In one embodiment of the present invention, a tubular collagen construct is lined with a monolayer of endothelial cells which constitutes the intima of blood vessel tissue equivalents. Outer layers can then be cast of smooth muscle cells in a collagen lattice, which constitutes the media of the blood vessel tissue equivalents. The smooth muscle cells contribute collagen, elastin, and other molecules to the matrix. In some embodiments, other extracellular matrix components such as hyaluronic acid are optionally added for particular applications. The outer layer of the blood vessel tissue equivalent can be fabricated from adventitial fibroblasts in a collagen lattice and constitutes the adventitia of the blood vessel tissue equivalent. A support member, e.g., a synthetic mesh, may also be optionally included in the blood vessel tissue equivalent, the mesh is typically in the collagen construct to strengthen the blood vessel tissue equivalent and facilitate suturing of a blood vessel equivalent to a native blood vessel. A removable, protective impermeable member, e.g., a plastic sleeve adjacent the abluminal surface may also be optionally provided.

It should be understood that the order of the layers in the blood vessel tissue equivalents in accordance with the present invention may be organized in the reverse order of that typically found in the natural blood vessel. For example, the endothelial cells which comprise the intima of normal blood vessels can be located so that they are on the outside of a tubular collagen construct.

Major advantages of collagen constructs of the present invention over previously described collagen constructs, particularly over the tissue equivalents described in the Patents, include variations of the physical properties of the construct to a greater degree by adjusting the fabrication conditions. Furthermore, the high concentration of collagen produces extremely strong collagen constructs which also provide excellent attachment for endothelial or epithelial cells. Furthermore, the methods of the present invention provide a greater control over the process to achieve the desired shape as well as the desired composition.

The collagen constructs of the present invention are useful as cell growth substrates and in the production of implantable prostheses and improved tissue equivalents.

DETAILED DESCRIPTION OF THE INVENTION

The present invention provides collagen constructs and methods of making such constructs. Although, the constructs and methods provided by the present invention will be illustrated through construction of tubular and flat collagen constructs, the invention is not so limited. It will be appreciated that the shape of such constructs is to be selected depending on the ultimate use of the construct.

The present invention provides methods of making collagen constructs. Such methods comprise the steps of:

(a) providing a solution comprising collagen adjacent a permeable member, the permeable member being in contact with a concentrating agent; and (b) maintaining the collagen solution, permeable member and concentrating agent under conditions sufficient to enable the collagen construct to form at the permeable member.

In the methods of the present invention a collagen solution is placed in contact with a permeable member which is in turn in contact with a concentrating agent. Such contact does not have to be direct in either case, e.g., a support member for the collagen construct may be disposed between the collagen solution and the permeable member. However, the contact must be sufficient to enable the selective mass transfer of solvent from the collagen solution and formation of the construct, e.g., in aqueous solutions the development of an osmotic gradient and formation of the construct.

In some particularly preferred embodiments, the foregoing method comprises the further step of causing fibrils to form in the collagen construct, either during or after formation thereof. In other particularly preferred embodiments, methods in accordance with the present invention include the further steps of cross-linking fibrils in the collagen construct. In yet other preferred embodiments, the method may also include the step of causing pores to form in the collagen construct, and/or texturizing one or more surfaces of the construct.

In another embodiment of the present invention, collagen constructs are formed by use of a device having an inner and outer chamber, the interface between the inner and outer chamber comprising a permeable member, the method comprising the steps of:

(a) providing a solution comprising collagen at a pH of about 2 to 4 to the outer chamber;

(b) providing a concentrating agent to the inner chamber; and (c) maintaining the collagen solution, permeable member and concentrating agent under conditions sufficient to enable the collagen construct to form at the permeable member.

Alternatively, the collagen solution may be provided to the inner chamber and the concentrating agent to the outer chamber to form a collagen construct at the inner surface of the permeable member.

The shape of the construct is determined in large part by the configuration of the permeable member. While the present invention will be illustrated by tubular and flat constructs, it will be appreciated that a wide range of configurations may be achieved by varying the shape of the permeable member and are contemplated by the teachings of the present invention. In one preferred embodiment of the present invention, tubular collagen constructs are formed by use of the foregoing device wherein the permeable member is tubular.

In some embodiments of the present invention, the construct production process is stopped and restarted with, e.g., a different collagen solution, to produce a layered construct. Accordingly, multi-layered collagen constructs of any desired shape are also provided by the present invention.

In another preferred embodiment, a multi-layer tubular collagen construct is made by use of a device having an inner and outer chamber, the interface between the inner and outer chamber comprising a tubular permeable member, the method comprising the steps of:

(a) providing a first solution comprising collagen at a pH of about 2 to 4 to the outer chamber;

(b) providing a concentrating agent to the inner chamber;

(c) maintaining the first collagen solution, permeable member and concentrating agent under conditions sufficient to enable the tubular collagen construct to form at the permeable member;

(d) replacing the first collagen solution with a second solution comprising collagen; and (e) maintaining the second collagen solution, permeable member and concentrating agent under conditions sufficient to enable a second tubular construct to form outwardly of the first tubular construct; and (f) repeating steps (d) and (e) if additional layers of tubular collagen construct are desired.

In yet other embodiments of the present invention the layers of the construct will range in composition and may further include, for example, angiogenic factors, anti-inflammatory agents, chemotatic agents and/or collagenase inhibitors.

The permeable member may be selected from any material which is compatible with collagen chemistry and which is substantially impermeable to collagen. Preferred permeable members include membranes and rigid porous members such as ceramic or stainless steel, having a pore size that substantially retains the collagen. When using a permeable member which is fairly flexible, e.g., dialysis tubing or nuclepore membrane, it is usually preferred to provide the collagen solution to the inner chamber, under a low hydrostatic pressure, in order to maintain the shape of the permeable member. However, if it is desired to provide the collagen solution to the outer chamber when using a flexible permeable member, the permeable member may be provided with a support member, e.g., a spring in the case of tubular constructs, to maintain the desired shape.

Collagen for use in the present invention may be obtained from any suitable source, typically skin and tendons, by procedures involving acid or enzyme extraction. A preferred collagen composition for use herein is obtained from a novel source, the common digital extensor tendon, by a novel extraction method, both as described in copending U.S. patent application Ser. No. 07/407,465, filed Sep. 15, 1989, now U.S. Pat. No. 5,106,9 which is incorporated herein by reference. Although both monomers and mixtures of monomers and fibrils of collagen can be used in the practice of the present invention, monomers are preferred for many applications.

Collagen solutions for use in present invention are generally at a concentration of about 5 to 10 mg/ml, at a pH of about 2 to 4, and may contain optional components such as neutral and charged polymers, including but not limited to, polyvinyl alcohol and hyaluromic acid. A preferred solvent for the collagen is dilute acetic acid, e.g., 0.05% to 0.1%. The collagen solution is monomeric or a mixture of monomer and higher ordered collagen polymers, e.g., dimers up to and including fibrils.

The collagen constructs of the present invention have a collagen concentration of about 50 to 100 mg/ml, more preferably about 100 mg/ml. However, concentrations outside this range may be preferred for some applications.

Fibrils are caused to form in the collagen construct either during or after formation thereof. In preferred embodiments fibrils are formed after the collagen concentration of the construct has reached about 50 to 100 mg/ml. Fibrils are caused to form by increasing the pH, the temperature or the salt concentration of the collagen construct, or a combination thereof as is illustrated in the Examples below. For example, increasing the pH to cause fibril formation can be achieved by gradual diffusion of salt from the concentrating agent through the permeable member and into the collagen solution (See Example 2 below) or by air drying the formed construct to evaporate the acid which has been trapped in the construct during formation (See Example 4 below). Air drying the formed collagen construct also causes the collagen concentration of the construct to increase. Such drying is carried out at a temperature and pH such that the collagen does not denature in any significant way.

In one particularly preferred method of fibril formation, the construct is removed from the device together with the permeable member at which it was formed, after the construct has reached a collagen concentration of about 50 to 100 mg/ml. The construct is then air dried overnight at 2-8° C. The pH gradually increases as the acid trapped in the construct during formation evaporates. The collagen construct is then rehydrated in isotonic saline, allowed to warm to 37° C. and separated from the permeable member. The method is shown in Example 4 below.

Collagen constructs are typically cross-linked after fibrils have been caused to form in the construct. This can be effected by any number of methods known to those of ordinary skill in the art including air-drying, lyophilization, or contact with an aldehyde, such as formaldehyde or glutaraldehyde. Cross-linking should be carried out so as to minimize embrittlement of the construct.

The burst strengths of tubular collagen constructs of the present invention, in which fibrils have been caused to form and have been cross-linked, are about 300 to 1000 mm Hg, preferably about 500 to 1000 mm Hg. Tubular constructs having a burst strength in excess of 1000 mm Hg are also formed by the methods of the present invention.

The burst strength of tubular collagen constructs of the present invention is further enhanced by incorporating a support member, such as a sythetic mesh, therein.

Concentrating agents for use in the present invention enable selective mass transfer of solvent from the collagen solution. In aqueous systems, such concentrating agents typically have a higher osmotic pressure than that of the collagen solution. Preferred concentrating agents include water soluble polymers such as polyethylene glycol or DEXTRAN. ® Salt solutions such as phosphate buffered saline ("PBS") are particularly preferred wherein the phosphate is at a concentration of about 0.001 to 0.02 M. The salt concentration of the concentrating agent in methods wherein the fibrils are caused to form as the construct forms at the permeable member are typically 0.07 to 0.30 M. This method is illustrated in Example 2 below wherein, a collagen construct is formed at a tubular permeable member comprising dialysis tubing or a tubular nuclepore membrane. One preferred concentrating agent comprises 20% w/v polyethylene glycol, molecular weight of 8,000, in PBS. Another preferred concentrating agent comprises 20% w/v DEXTRAN® in PBS.

In embodiments wherein fibrils are caused to form after the construct has formed, the concentrating typically comprises a biocompatible polymer at a concentration of about 5 to 20%, phosphate buffers at about 0.001 to 0.2 M and sodium chloride at about 0.075 to 0.15 M. It is expected that both lower and higher concentrations of sodium chloride will be useful in this embodiment of the present invention.

In embodiments wherein the collagen constructs of the present invention are provided with pores, this can be accomplished by a number of ways known to those of ordinary skill in the art, including incorporation of a polymer in the construct. Such polymers are soluble in solvents which do not act on the collagen construct to any significant detrimental degree. Pores are formed as the polymer is dissolved from the construct using solvents in which the polymer but not the collagen construct is soluble. Polyvinyl alcohol, one preferred polymer for pore formation, is dissolved from the collagen construct by use of water. Pores may also be formed by lyophilization of the collagen construct.

Collagen constructs of the present invention can be "textured" if desired, e.g., by mechanically imprinting patterns or by acid etching. Texturing of the constructs may be desired in certain instances, e.g., to promote adherence, growth and/or invasion of seeded cells. Such texturing is typically carried out before cross-linking the collagen fibrils.

In some embodiments of the present invention, collagen constructs may further comprise a reinforcing means to increase structural integrity, e.g., a synthetic mesh, to facilitate suturing. Particularly preferred reinforcing means include meshes comprising one or more polyesters, such as E.I. DuPont de Nemour's DACRON® or DACRON®/LYCRA® combination. Furthermore, collagen constructs in accordance with the present invention are optionally provided with components to confer desired properties, and may include components not typically found in normal tissues or organs.

In one preferred embodiment, such constructs include one or more cell types. Typically, such cells are included in the construct after formation thereof by seeding one or more surfaces of the construct with the desired cell type or types, including but not limited to endothelial and epithelial cells. In the case of multilayered collagen constructs, cells are seeded between layers, if desired. In one particularly preferred embodiment of the present invention, collagen constructs are populated with cells to form living tissue equivalents.

Tissue equivalents, including blood vessel and skin tissue equivalents, will be used in a non-limiting way to exemplify collagen constructs of the present invention which have been provided with cells.

Figures 1, 2:
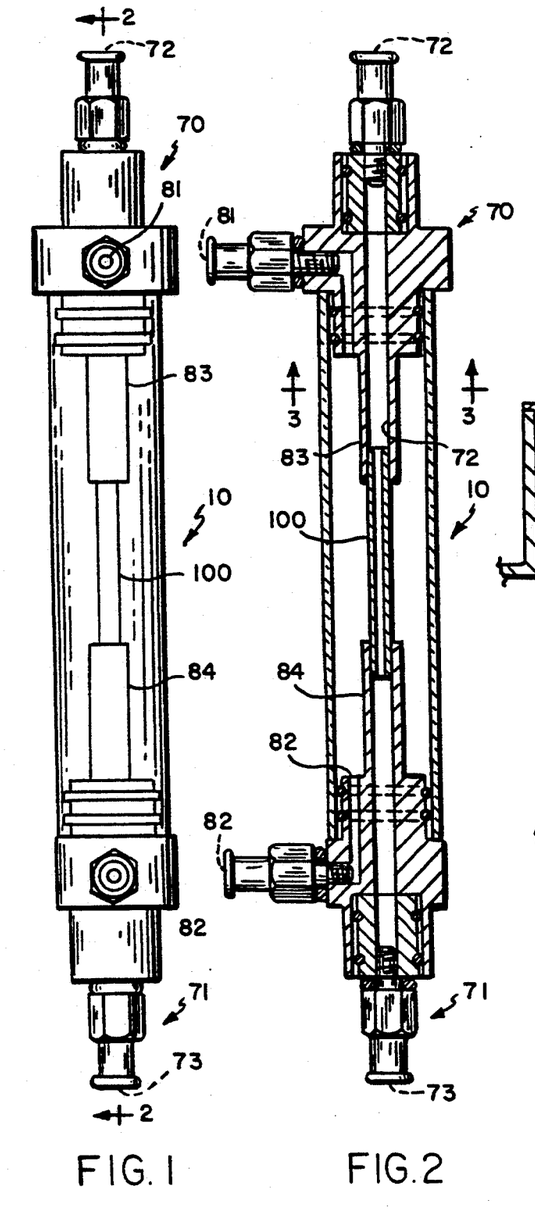
FIG. 1 is a plan view of one apparatus for use in the present invention.
FIG. 2 is a section on line 2—2 of the apparatus of FIG. 1.
Figure 3:
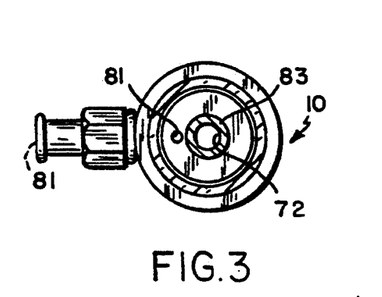
FIG. 3 is a section on line 3—3 of the apparatus of FIG. 2.

Referring to the drawings, FIGS. 1, 2 and 3 show one apparatus for use in the present invention in the formation of tubular collagen constructs. The apparatus comprises a cylindrical container 10, the container being sealably closed by cover means 70,71. A hollow mandrel 100 comprising a permeable member is disposed in the container 10 and positioned therein by means of hollow support members 83, 84 which in turn are removably connected to the cover means 70, 71, respectively. Cover means 70, 71 are provided with ports 72, 73, which in turn are engaged with hollow support members 83, 84 during use. Means (not shown) for providing a concentrating agent (not shown) to the hollow mandrel 100 through ports 72,73 are also present and typically comprise a pump means connected to a reservoir of concentrating agent for pumping concentrating agent through the mandrel 100.

Cover means 70, 71 are also provided with port means 81, 82 which open into the container 10 when the apparatus is assembled for use. Means (not shown) for providing a collagen solution to the container 10 through ports 81, 82 are also present and typically comprise a reservoir filled with collagen solution which is connected to ports 80, 81.

In one embodiment, tubular collagen constructs in accordance with the present invention are formed by use of the apparatus shown in FIGS. 1, 2 and 3 as follows: A solution comprising collagen in dilute acetic acid is added to container 10 via ports 81, 82 which are connected to a collagen reservoir (not shown) which replaces solution volume as the collagen concentrates at the permeable member 100 to form a tubular collagen construct. A concentrating agent is provided to the lumen of the mandrel 100 via ports 72, 73 which are connected to means for providing a concentrating agent to the apparatus. Negative pressure differential between the collagen solution and the concentrating agent is achieved by pulling the concentrating agent through the mandrel 100. If positive pressure is used, the concentrating agent may be forced out of the mandrel 100. The apparatus and its contents are maintained under conditions, sufficient to enable the collagen construct to form at the mandrel 100, typically continued at 2-8° C. for 3-5 days until the construct reaches a thickness of about 2 mm. The mandrel is removed together with the collagen construct and air dried overnight to further concentrate the collagen and to cause fibrils to form in the tubular collagen construct by means of evaporating the acetic acid trapped in the construct to thereby raise the pH. The dried tubular collagen construct having a thickness of about 0.5 to 1 mm is then rehydrated in isotonic PBS and removed from the mandrel. The collagen construct is then seeded with appropriate cells to form a blood vessel equivalent.

The apparatus of FIGS. 1, 2 and 3 can also be used to form collagen constructs at the inner surface of the hollow mandrel 100 by providing collagen solution thereto through ports 72, 73 and concentrating agent to the container 10 through ports 81, 82.

In yet another embodiment of the present invention (not illustrated in the Figs.), a collagen construct is formed at the inner or outer surface of a flexible permeable member such as a nuclepore membrane or dialysis tubing. For example, collagen (2.5 mg/ml in 0.05% acetic acid) is poured into a permeable tube (either dialysis membrane or nuclepore filter membrane glued into a cylinder) the tube (typically 3-8 mm in diameter) is sealed at one end or fit with a collagen recirculating loop. The collagen in the tube is placed under positive pressure (either hydrostatic or pump) and placed into a solution of polyethylene glycol or DEXTRAN® in PBS. This is typically maintained overnight at 2-8° C. If wider diameter tubing is used, the tubular collagen construct can be cut open and used as a sheet.

Figure 4:
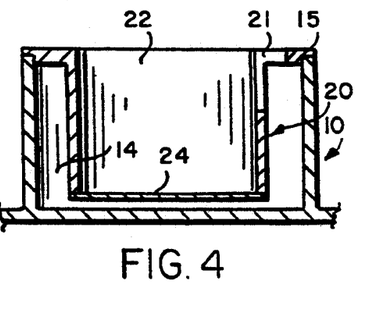
FIG. 4 is a cutaway view of another apparatus for use in the present invention.

Referring to the drawings, FIG. 4 shows another apparatus for use in the present invention. The apparatus comprises a device having an outer container 10 and an inner container 20. The inner container 20 is provided with a rim 15 to provide means for positioning the inner container 20 in the outer container 10 thereby defining an outer area 14 and an inner area 22. The inner container 20 is provided with a permeable member 24. The permeable member 24 is sealably attached to the inner container 20 to form the bottom surface thereof. The container 10 is provided with at least one opening 21 which provides access to the outer area 14. The apparatus shown in FIG. 4 is typically used for making flat collagen constructs.

In accordance with the present invention, a concentrating agent is provided to the outer container 10 and a collagen solution is provided to the inner container 20. A sufficient volume of concentrating agent is provided to the outer container 10 so that the concentrating agent contacts the permeable member. If desired, concentrating agent can be replaced during formation of the collagen construct by means of opening 21. The apparatus and its contents are then maintained under conditions which enable formation of a collagen construct, in accordance with the present invention. Such constructs may then be seeded with cells to form a tissue equivalent, e.g., keratinocytes to form a skin tissue equivalent.

In some embodiments the outer chamber 10 is provided with inlet means and outlet means so that the concentrating agent can be replaced or circulated with ease.

The collagen constructs of the present invention have been successfully implanted in mammals using standard surgical techniques. In one study, sheep blood vessel equivalents made by use of a collagen construct in accordance with the present invention were implanted as an interposition graft in the superficial femoral artery of sheep. The blood vessel tissue equivalents were produced by providing endothelial cells on the luminal surface and smooth muscle cells on the abluminal surface of tubular collagen constructs produced by the teachings of the present invention. Such blood vessel tissue equivalents were typically about 5 cm long with an inside diameter of about 0.45 mm. The thickness of such blood vessel tissue equivalents upon implantation ranged from about 0.3 to about 0.7 mm.

Such blood vessel tissue equivalent implants have been maintained in place for up to thirty days and have remained patent as shown by angiogram and Doppler ultrasound, techniques well known to one of ordinary skill in the art. Upon removal after thirty days, the implant had only a small platelet-fibrin deposit on the surface.

The invention will be further understood with reference to the following examples which are purely exemplary in nature and are not meant to be utilized to limit the scope of the invention.

An apparatus similar to that shown in FIGS. 1-3 was used in the following examples.

EXAMPLE 1

Preparation of Collagen Construct Formed Around a Porous Member and Dried at Room Temperature.

1. The apparatus was maintained in a vertical position, i.e., cover means 70 is at the top and cover means 71 is at the bottom of the apparatus during the formation of the construct. The outer chamber 10 containing a 4.5 mm diameter porous ceramic mandrel with a pore size of 1.5 μm (Coors Ceramics Co.) was filled with 2.5 mg/ml collagen in 0.05% acetic acid at 2-8° C. prepared as described in U.S. patent application Ser. No. 07/407,465, filed Sep. 15, 1989.

2. A reservoir containing approximately 60 ml of collagen was then attached to the upper port 81. The function of this reservoir is to replace volume lost as the collagen construct forms.

3. 200 ml of a solution of 20% polyethylene glycol MW 8000 (Sigma Chemical Co.) in isotonic phosphate buffered saline at 2-8° C. was then circulated under reduced pressure through the ceramic mandrel for 96 hours at 2-8° C.

4. The apparatus was then dismantled and the mandrel containing the collagen construct carefully removed and left to dry for 18-24 hours at room temperature.

5. The collagen construct was then rehydrated in isotonic saline at room temperature for at least 2 hours.

6. The rehydrated collagen construct was then carefully removed from the porous ceramic mandrel by eversion.

7. The burst strength of collagen constructs formed as described above was compared with the burst strength of blood vessel equivalents formed in accordance with the Patents (hereinafter "BVE"). The results of one such test showed burst strengths of 750, 460 and 760 mm Hg, respectively, for the constructs compared with 310 mm Hg for the BVE.

EXAMPLE 2

Preparation of a Collagen Construct Formed Within a Porous Member Using Polyethylene Glycol at Neutral pH and Dried at Room Temperature.

1. A 5 mm diameter cylinder of polycarbonate membrane (pore size 5 μm) (Nucleopore Corp.) was formed by placing the membrane around a 5 mm glass rod and heat welding a seam using an impulse sealer (TEW Electric Heating Equipment Co., Inc.).

2. The cylinder was sealed at one end by luer fittings and the other end was connected to a 6 ml reservoir of 2.5 mg/ml collagen in 0.05% acetic acid at 2-8° C.

3. The collagen was allowed to fill the cylinder and is placed upright in a flask containing 6 L of 20% polyethylene glycol MW 8000 (Sigma Chemical Co.) in isotonic phosphate buffered saline, pH 7 at 2-8° C.

4. The polyethylene glycol was circulated using a magnetic stir bar and motor. The apparatus was maintained at 2-8° C. for 36 hours.

5. The membrane was carefully removed and a 3 mm glass rod inserted inside of the formed tubular collagen construct.

6. The collagen tube was allowed to dry for 18-24 hours at room temperature.

7. The collagen construct was rehydrated in isotonic phosphate buffered saline at room temperature for at least 2 hours.

8. The rehydrated collagen construct was then carefully removed from the porous ceramic mandrel by eversion.

9. The burst strength of collagen constructs formed as described above were tested and compared with blood vessel equivalents (BVE) formed in accordance with the Patents. The results one such test showed burst strengths of 700, 480, and 800 mm Hg, respectively, for three constructs, as compared with a burst strength of 310 mm Hg for the BVE.

EXAMPLE 3

Preparation of Collagen Construct Formed Within a Porous Member and Dried at 2-8° C.

1. The construct was prepared as described in Example 2 except that the 20% polyethylene glycol was in an isotonic solution of 0.05% acetic acid.

EXAMPLE 4

Preparation of Collagen Construct Formed Around a Porous Member and Dried at 2-8° C.

1. The collagen construct was prepared as described in Example 1, steps 1-3.
2. The collagen construct was allowed to dry for 18-24 hours at 2-8° C.
3. The collagen construct was then rehydrated in isotonic saline for 18-24 hours at 2-8° C.
4. The rehydrated collagen construct was then allowed to warm to 37° C. for 8 hours.
5. The rehydrated collagen construct was then carefully removed from the porous ceramic mandrel by eversion.

EXAMPLE 5

Preparation of Collagen Construct Formed Within a Porous Member and Dried at 2-8° C.

1. The collagen construct was prepared as described in Example 2, steps 1-3, or by Example 3.
2. The collagen construct was allowed to dry for 18-24 hours at 2-8° C.
3. The collagen construct was then rehydrated in isotonic saline for 18-24 hours at 2-8° C.
4. The rehydrated collagen construct was then allowed to warm to 36° C. for 8 hours.
5. The porous member was then carefully removed.

EXAMPLE 6

Production of Porous Collagen Constructs By Lyophilization.

Collagen constructed formed according to: Example 1, steps 1-3, Example 2, steps 1-5, Example 3, and Example 4, steps 1-5 can be dried by freezing the construct to −20° C. and drying by lyophilization (The Virtis Co., Inc.).

EXAMPLE 7

Production of Porous Collagen Constructs by Incorporation of Polyvinyl Alcohol.

The collagen construct was made as described in Example 1, except that the collagen solution was supplemented with 10 mg/ml Mono-Sol series 7-000 polyvinyl alcohol (Chris-Craft Industrial Products, Inc.). The polyvinyl alcohol was removed from the construct to form pores therein by treatment of the construct with water.

EXAMPLE 8

Production of Collagen Construct Having a Mesh Support Member.

Such constructs were produced as described in Example 1-5, except that a DACRON® mesh was slipped over the mandrel in Examples 1 and 4 above or held within the permeable member in Examples 2, 3 and 5. The mesh diameter preferably matched the size of the permeable member and was in close contact with it. The mesh was then incorporated in the body of the collagen construct.

Collagen constructs were prepared as in Example 1 and 2 above, with the further inclusion of a mesh. The burst strength of such constructs have been tested and the results of three such tests are compared with the burst strength of a BVE. Three constructs prepared per Example 1 plus a mesh showed burst strengths of 840, 750 and 550 mm Hg, respectively. Two constructs prepared per Example 2 plus a mesh showed burst strengths of 460 and 530 mm Hg. In comparison, the BVE showed a burst strength of 310 mm Hg.

EXAMPLE 9

Seeding a Collagen Construct with Cells to Form a Blood Vessel Equivalent.

Collagen constructs have been formed in accordance with Examples 1 and 2 above and then seeded with cells by a method similar to that described below:

1. The rehydrated collagen construct was assembled in an apparatus similar to that shown in FIGS. 1-3 in place of the permeable member 100 and secured in place with silk sutures.
2. The abluminal space was filled with a suspension of sheep smooth muscle cells ($2 \times 10^5$/ml) in MCDB-107 media (Hazelton Labs.) with 2% serum, 1% glutamine, 5 ug/ml insulin, 0.1 ug/m heparin binding growth factor-1 (Upstate Biomedical), 0.5% penicillin/streptomycin, 10 ug/ml transferrin.
3. The mold was rotated for 24 hours at 0.5 rpm at 37° C.
4. The lumen was seeded with endothelial cells at $1 \times 10^5$/cm$^2$ as a suspension in MCDB-107, 10% serum, 1% glutamine, 0.5% pencillin/streptomycin, 5 ug/ml insulin, 0.1 ug/ml heparin binding growth factor-1, and 10 ug/ml transferrin.
5. The mold was rotated for 3 hours at 0.5 rpm.
6. A medium containing MCDB-107, 10% serum, 1% glutamine, 0.5% pencillin/streptomycin, 5 ug/ml insulin, 0.1 ug/ml heparin binding growth factor-1, and 10 ug/ml transferrin was then prefused through the lumen at 0.3 ml/min for at least 48 hours.

Such blood vessel tissue equivalents have been implanted in sheep as described above.

It is understood that the examples and embodiments described herein are for illustrative purposes only, and that various modifications or changes in light thereof that will be suggested to persons skilled in the art are to be included in the spirit and purview of this application and the scope of the approved claims.

What is claimed is:

1. A method of forming a construct comprising collagen, the method comprising the steps of:
   (a) providing an aqueous solution comprising collagen adjacent a permeable member, the permeable member being substantially impermeable to collagen and in contact with a concentrating agent, wherein the concentrating agent has an osmotic pressure higher than that of the collagen solution and permits selective mass transfer of solvent from the collagen solution through the permeable member; and
   (b) maintaining the collagen solution, permeable member and concentrating agent under conditions sufficient to enable the selective mass transfer of solvent from the collagen solution and the formation of the collagen construct at the permeable member.

2. The method of claim 1, further comprising the step of causing fibrils to form in the collagen construct.

3. The method of claims 1 or 2, wherein the concentrating agent comprises a water-soluble polymer.

4. The method of claim 3, wherein the concentrating agent comprising at least one of polyethylene glycol and dextran.

5. The method of claim 3, wherein the concentrating agent comprises a polymer in phosphate buffered saline.

6. The method of claim 5, wherein the concentrating agent comprises a solution of polyethylene glycol or dextran in sodium chloride.

7. The method of claim 6, wherein the concentrating agent comprises a solution of 20% weight/volume polyethylene glycol having a molecular weight of about 8000 in phosphate buffered saline.

8. The method of claim 2, wherein the concentrating agent comprises a polymer in phosphate buffered saline, and the fibrils are caused to form by means of increasing the pH and ionic strength of the concentrating agent.

9. The method of claims 1 or 2, wherein the collagen concentration of the construct is about 50 to 100 mg/ml.

10. The method of claims 1 or 2, wherein the collagen concentration of the construct is at least about 100 mg/ml.

11. The method of claims 1 or 2, wherein the permeable member comprises a membrane.

12. The method of claim 11, wherein the membrane comprises a porous ceramic or stainless steel material, dialysis tubing, or a nucleopore membrane.

13. The method of claims 1 or 2, wherein the permeable member is flat or tubular.

14. The method of claims 1 or 2, further comprising the step of providing cells to the collagen construct.

15. The method of claim 14, wherein the cells are at least one of endothelial and epithelial cells.

16. The method of claims 1 or 2, further comprising the step of forming pores in the collagen construct.

17. The method of claim 16, wherein pores are formed by lyophilyzing the collagen construct.

18. The method of claim 16, wherein the pores are formed by means of incorporating a polymer in the collagen construct and the method further comprises the step of removing the polymer from the collagen construct.

19. The method of claim 18, wherein the polymer is polyvinyl alcohol or hyaluronic acid.

20. The method of claim 2, further comprising the step of cross-linking the fibrils in the collagen construct.

21. The method of claim 20, wherein the fibrils are cross-linked by air-drying, lyophilizing or contact with an aldehyde.

22. The method of claim 20, wherein the collagen construct has a burst strength of about 300 to 1000 mm Hg.

23. The method of claim 20, wherein the collagen construct has a burst strength of greater than 1000 mm Hg.

24. The method of claims 1 or 2, wherein the collagen solution is at a concentration of about 5 to 10 mg/ml collagen and a pH of about 2 to 4.

25. The method of claims 1 or 2, wherein the collagen construct is provided with a support member.

26. The method of claim 25, wherein the support member comprises a polyester.

27. The method of claims 1 or 2, wherein the collagen solution further comprises at least one of an angiogenic factor, an anti-inflammatory agent, a chemotactic agent, or a collagenase inhibitor.

28. A method of forming a tubular collagen construct in accordance with claims 1 or 2 by use of a device having an inner and outer chamber, the interface between the inner and outer chamber comprising a tubular permeable member, the method comprising the steps of:
  (a) providing the solution comprising collagen the outer chamber;
  (b) providing the concentrating agent to the inner chamber; and
  (c) maintaining the collagen solution, permeable member and concentrating agent under conditions sufficient to enable the collagen construct to form at the permeable member.

29. A method of forming a tubular collagen construct in accordance with claims 1 or 2 by use of device having an inner and outer chamber, the interface between the inner and outer chamber comprising a tubular permeable member, the method comprising the steps of:
  (a) providing the solution comprising collagen to the inner chamber;
  (b) providing the concentrating agent to the outer chamber; and
  (c) maintaining the collagen solution, permeable member and concentrating agent under conditions sufficient to enable the collagen construct to form at the permeable member.

30. A method of forming a multi-layer tubular collagen chamber, the interface between the inner and outer chamber comprising a tubular permeable member, the method comprising the steps of:
  (a) providing a first solution comprising collagen at a pH of about 2 to 4 to the outer chamber;
  (b) providing a concentrating agent to the inner chamber;
  (c) maintaining the first collagen solution, permeable member and concentrating agent under conditions sufficient to enable the tubular collagen construct to form at the permeable member;
  (d) replacing the first collagen solution with a second solution comprising collagen; and
  (e) maintaining the second collagen solution, permeable member and concentrating agent under conditions sufficient to enable a second tubular construct to form outwardly of the first tubular construct; and
  (f) repeating steps (d) and (e) if additional layers of tubular collagen construct are desired.

31. The method of 30, further comprising the step of causing fibrils to form in at least one layer of the collagen construct.

32. A method of forming a flat collagen construct by use of a device having an inner and outer container, the interface between the inner and outer chamber comprising a flat permeable member, the method comprising the steps of:
  (a) providing a solution comprising collagen to the inner chamber;
  (b) providing a concentrating agent to the outer chamber; and
  (c) maintaining the collagen solution, permeable member and concentrating agent under conditions sufficient to enable the flat construct to form at the permeable member.

33. A method of concentrating a solution of collagen comprising:

(a) contacting a collagen solution with a permeable member, the permeable member being in contact with an agent for concentrating the collagen;
(b) maintaining the collagen solution and concentrating agent under conditions sufficient to enable the collagen solution to reach a concentration of, from about 50 to 100 mg/ml.

34. The method of claim 33, wherein the collagen solution reaches a concentration of about 100 mg/ml.

* * * * *